(12) United States Patent
Wich et al.

(10) Patent No.: US 8,216,573 B2
(45) Date of Patent: *Jul. 10, 2012

(54) PROCESS FOR THE FERMENTATIVE PRODUCTION OF ANTIBODIES

(75) Inventors: Guenter Wich, Munich (DE); Tobias Dassler, Munich (DE)

(73) Assignee: Wacker Chemie AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/859,200

(22) Filed: Sep. 21, 2007

(65) Prior Publication Data

US 2008/0206818 A1    Aug. 28, 2008

(30) Foreign Application Priority Data

Sep. 22, 2006 (EP) .................................... 06121093

(51) Int. Cl.
*C12N 1/20* (2006.01)
*C12P 21/04* (2006.01)

(52) U.S. Cl. ................. 424/133.1; 435/69.6; 435/252.33

(58) Field of Classification Search ............... 424/133.1; 435/69.6, 252.33
See application file for complete search history.

(56) References Cited

U.S. PATENT DOCUMENTS

| | | | |
|---|---|---|---|
| 4,643,969 A * | 2/1987 | Inouye et al. ................ | 435/69.1 |
| 5,573,929 A | 11/1996 | Misawa et al. | |
| 5,693,493 A | 12/1997 | Robinson et al. | |
| 5,919,895 A | 7/1999 | Schmid et al. | |
| 6,514,730 B1 | 2/2003 | Schmid et al. | |
| 2003/0073164 A1 | 4/2003 | Simmons et al. | |
| 2003/0096343 A1 | 5/2003 | Robinson | |
| 2005/0089519 A1 | 4/2005 | Kipriyanov et al. | |
| 2005/0163708 A1 | 7/2005 | Robinson | |
| 2005/0170464 A1 | 8/2005 | Simmons | |
| 2007/0020725 A1 | 1/2007 | Simmons | |
| 2007/0065909 A1 | 3/2007 | Simmons | |
| 2008/0076158 A1 * | 3/2008 | Dassler et al. ................ | 435/71.2 |
| 2008/0254511 A1 * | 10/2008 | Dassler et al. ................ | 435/69.4 |

FOREIGN PATENT DOCUMENTS

| | | |
|---|---|---|
| EP | 0300459 | 1/1989 |
| EP | 0 338 410 A2 | 10/1989 |
| EP | 0 497 757 A | 8/1992 |
| EP | 0 497 757 B1 | 6/1994 |
| EP | 0 448 093 B1 | 3/1996 |
| EP | 0 677 109 B1 | 4/2000 |
| JP | 2991720 B2 | 12/1999 |
| JP | 2004530419 A | 10/2004 |
| WO | WO 91/06655 | 5/1991 |
| WO | 93/06217 * | 4/1993 |
| WO | 9307896 | 4/1993 |
| WO | WO 93/06217 * | 4/1993 |
| WO | 9409817 | 5/1994 |
| WO | WO 02/061090 A2 | 8/2002 |
| WO | WO 2005/038031 A1 | 4/2005 |

OTHER PUBLICATIONS

Ibragimova and Eade (Biophysical Journal, Oct. 1999, vol. 77, pp. 2191-2198).*
Better et al. (Proc. Natl. Acad. Sci. 90:457-461, 1993).*
Binder et al. (Gene 47:269-277, 1986).*
*E. coli* Genetic Stock Center CGSC (search for E610; pp. 1-2 (Jun. 1, 2009)).*
Better et al. (Proc. Natl. Acad. Sci. 90:457-461, 1993.*
Choi and Lee et al., Secretory and extracellular production of recombinant proteins using *Escherichia coli*, Appl. Microbiol. Biotechnol., 2004, pp. 625-635, v. 64.
Shokri et al., Cell and process design for targeting of recombinant protein into the culture medium of *Escherichia coli*, Appl. Microbiol. Biotechnol., 2003, pp. 654-664.
Simmons et al., Expression of full-length immunoglobulins in *Escherichia coli*: rapid and efficient production of aglycosylated antibodies, J. of Immunological Methods, 2002, pp. 133-147.
Leonhartsberger, S. "*E. coli* Expression System Efficiently Secretes Recombinant Proteins into Culture Broth," BioProcess International, p. 2-4, Apr. 2006.
Rumbley, C.A. et al., "Lupus-derived autoantibodies with dual autoactivity: anti-DNA and anti-Fe. I. Comparison of IgG autoreactivities with single-chain Fv derivatives," Clin Exp Immunol, 102, p. 341-348, 1995.
Bourret, R.B. et al., "Intermediates in Bacteriophage Mu Lysogenization of *Escherichia coli* him Hosts," Journal of Bacteriology, vol. 170, p. 1683-1690, 1988.
Denzin, L.K. et al., "Single-chain Site-specific Mutations of Fluorescein-Amino Acid Contact Residues in High Affinity Monoclonal Antibody 4-4-20," Journal of Biological Chemistry, vol. 266, p. 14095-14103, 1991.
Pack, P. et al., "Improved Vibalent Miniantibodies, with Identical Avidity as Whole Antibodies, Produced by High Cell Density Fermentation of *Escherichia coli*," Bio/Technol. vol. 11, p. 1271-1277, 1993.
Robbens, J. et al., "Improved periplasmic production of biologically active murine interleukin-2 in *Escherichia coli* through a single amino acid change at the cleavage site," Proc Biochem 41, issue 6, p. 1343-1346, Jun. 2006.
Guzman, C. et al., "Export of *Bordetella pertussis* serotype 2 and 3 fimbrial subunits by *Escherichia coli*," FEMS Microbiol Lett, 128, p. 189-194, 1995.
Khushoo, A. et al., "Optimization of extracellular production of recombinant asparaginase in *Escherichia coli* in shake-flask and bioreactor," Appl Microbiol Biotechnol, 68, p. 189-197, 2005.

(Continued)

*Primary Examiner* — Lynn Bristol
(74) *Attorney, Agent, or Firm* — Brooks Kushman P.C.

(57) ABSTRACT

The present invention relates to a process for producing a correctly folded and assembled full-length antibody using an *E. coli* strain, which comprises fermenting an *E. coli* strain which leaks periplasmic proteins into the medium, comprising a gene coding for the heavy chain of an antibody functionally linked to a signal sequence coding for a signal peptide, and a second gene coding for the light chain of an antibody, functionally linked to a signal sequence coding for a signal peptide, in a culture medium, where the *E. coli* strain secretes a full-length antibody into the culture medium, and the full-length antibody is removed from the culture medium.

14 Claims, 2 Drawing Sheets

OTHER PUBLICATIONS

Yang, J. et al., "One Hundred Seventy-Fold Increase in Excretion of an FV Fragment-Tumor Necrosis Factor Alpha Fusion Protein (sFV/TNF-α) from *Escherichia coli* Caused by the Synergistic Effects of Flycine and Triton X-100," Appl Env Microbiol, 64, p. 2869-2874, 1998.

Lee J.H. et al., "Production of Human Leukoycte Interferon on *Escherichia coli* by Control of Growth Rate in Fed-Batch Fermentation," Biotechnol Lett, vol. II, p. 695-698, 1989.

Lee, K. et al., "Fermentor Production of HBsAg Via Expression in the Periplasmic Space of *E. coli*," in Horizons of Biochemical Engineering, edited by S. Aiba, Oxford University Press, p. 125-134, 1988.

Chames, P et al., "Production of a Soluble and Active MBP-scFv fusion: favorable effect of the leaky toIR strain," FEBS Lett., 405, p. 224-228, 1997.

Arbabi-Ghahroudi, M. et al., "Prokaryotic expression of antibodies," Cancer and Metastasis Reviews, 24, p. 501-519, 2005.

Plückthun, A. et al., "Producing antibodies in *Escherichia coli*: From PCR to fermentation," Antibody Engineering, J. McCafferty, H.R. Hoogenboom and D.J. Chiswell, Eds. (IRL Press, Oxford, 1996) p. 203-252 (reprint).

Shibui, T. et al., "Secretion of a functoinal Fab fragment in *Escherichia coli* and the influence of culture conditions," Appl Microbiol Biotechnol, 37, p. 352-357, 1992.

Nagahari, K. et al., "Secretion into the culture medium of a foreign gene product from *Escherichia coli*: use of the ompF gene for secretion of human β-endorphin," The EMBO Journal, vol. 4, p. 3589-3592, 1985.

\* cited by examiner

Fig. 1: Cloning vector pJF118ut
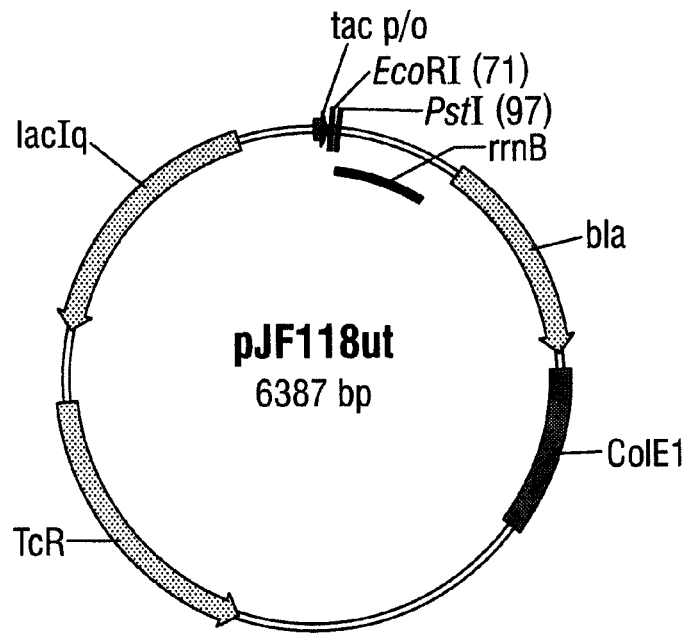
Fig. 2: Plasmid pHC-anti-TF
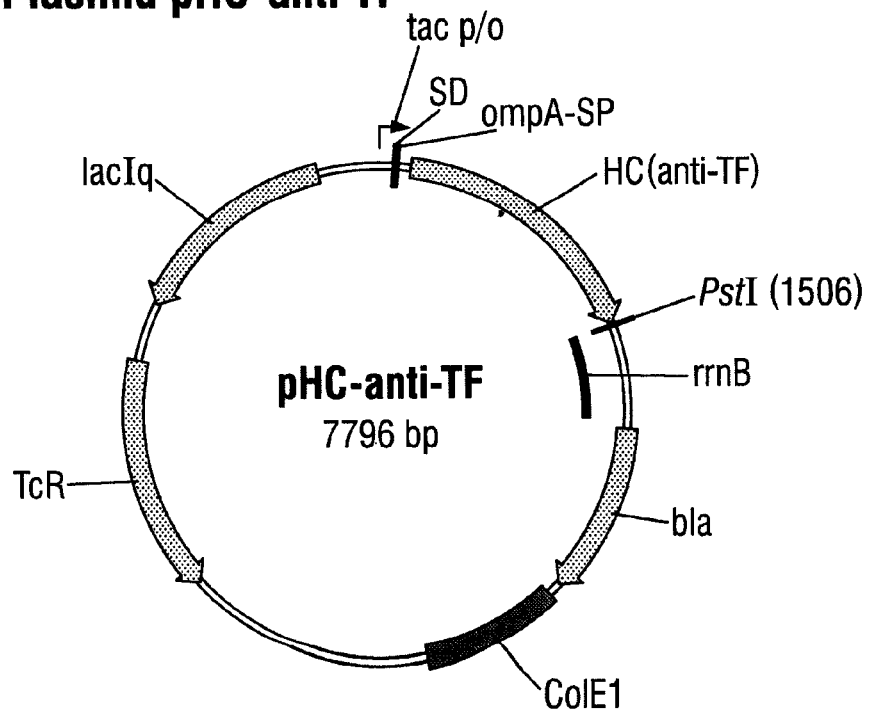

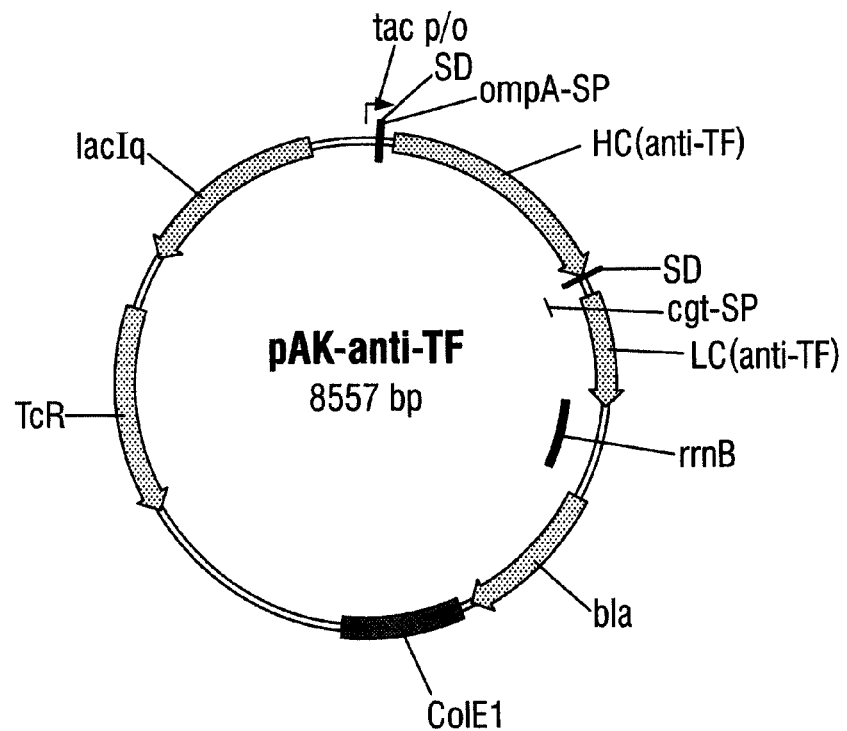
Fig. 3: Anti-TF antibody expression plasmid pAK-anti-TF

PROCESS FOR THE FERMENTATIVE PRODUCTION OF ANTIBODIES

BACKGROUND OF THE INVENTION

1. Field of the Invention

The invention relates to a process for the fermentative production of full-length antibodies using *Escherichia coli* strains able to release proteins into the fermentation medium.

2. Background Art

The market for recombinant protein pharmaceuticals (biologics) has grown greatly in recent years. However, because the production costs for protein-based active pharmaceutical ingredients are still very high, there is a continual search for more efficient and more cost-effective processes and systems for producing them.

A particularly important class of proteins is antibodies. Antibodies are employed in research, in diagnosis and as therapeutic agent on a large scale, so that there is a need for production processes, which are particularly efficient and possible on the industrial scale.

In the case of antibodies, a distinction is made between full-length antibodies and antibody fragments. Full-length antibodies consist of four protein chains, two identical heavy chains and two identical light chains. The various chains are linked together by disulfide bridges. Each heavy chain is composed of a variable region ($V_H$) and of a constant region, which includes the three domains CH1, CH2 and CH3. The region of the heavy chain which includes the CH2 and CH3 domains and which is also referred to as Fc region is not involved in antigen binding, but has other functions such as, for example, activation of the complement system. Each light chain is composed of a variable region ($V_L$) and of a constant region, which includes the $C_L$ domain.

Antibodies (immunoglobulins) are assigned to five classes depending on the amino acid sequence of the heavy chain: IgA, IgD, IgE, IgG and IgM. The term full-length antibody means all antibodies in which the light chains in each case include the $V_L$ and $C_L$ domains, and the heavy chains are substantially composed of the $V_H$-CH1-CH2-CH3 domains. Therefore, the antibody is able to carry out other functions (e.g. activation of the complement system), besides being able to bind a specific antigen.

By contrast, antibody fragments consist of only parts of a full-length antibody, normally the part including the antigen binding sites.

The organism most frequently used at present for producing recombinant proteins is the gram-negative enterobacterium *Escherichia coli*, because its genetics and physiology have been very well investigated, the generation time is short and manipulation is easy. This organism is likewise used to produce antibody fragments.

In contrast to antibody fragments, there have to date been only very few attempts to produce full-length antibodies in *E. coli*. Because of the size and complex structure of full-length antibodies, it is difficult to obtain correctly folded and assembled antibodies. Cytoplasmic production in *E. coli* is not possible in this case because *E. coli* does not form disulfide bridges in the cytoplasm. WO02/061090 describes the periplasmic production of full-length antibodies in *E. coli*. For this purpose, a specially designed expression vector on which the light chain and the heavy chain are expressed independently of one another in different promoter-cistron pairs is used. The two chains are in this case each fused to signal peptides and are transported by the usual Sec pathway in *E. coli* into the periplasm, where the folding and assembling takes place. To obtain the antibodies in this case it is necessary to disrupt the cells. The yields do not exceed 156 mg/l. Higher yields up to 880 mg/l were achieved only when periplasmic folding assistants (chaperones), such as the dsb proteins or FkpA, were coexpressed on plasmids in addition to the antibody chains. It is necessary to purify the antibodies from the large number of other *E. coli* proteins.

This process has the disadvantage for the industrial production of antibodies that the *E. coli* cells must be disrupted, and the target protein must be purified from the large number of other *E. coli* proteins. Any coexpression of periplasmic chaperones impedes this purification even further through the considerable additional amounts of unwanted proteins.

SUMMARY OF THE INVENTION

It was an object of the present invention to provide a process that makes it possible to produce a correctly folded and assembled full-length antibody and is not associated with the prior art disadvantages. This object is achieved by a process which comprises fermenting an *E. coli* strain which releases periplasmic proteins into a medium, comprising a gene coding for the heavy chain of an antibody functionally linked to a signal sequence coding for a signal peptide, and a second gene coding for the light chain of an antibody, functionally linked to a signal sequence coding for a signal peptide, in a culture medium, where the *E. coli* strain secretes a full-length antibody into the culture medium. The full-length antibody is removed from the culture medium.

BRIEF DESCRIPTION OF THE DRAWINGS

FIG. 1 shows the cloning vector pJF118ut from the example.

FIG. 2 shows the plasmid pHC-anti-TF from the example.

FIG. 3 shows the anti-TF antibody expression plasmid pAK-anti-TF from the example.

The abbreviations used in the figures have the following meaning:
tac p/o: tac promoter/operator
rrnB: terminator
bla: β-lactamase gene (ampicillin resistance)
ColE1: origin of replication
TcR: tetracycline resistance
lacIq: repressor of the tac promoter
SD: Shine-Dalgarno sequence
ompA-SP: ompA signal peptide
HC (Anti-TF): reading frame of the heavy chain of the anti-TF antibody
cgt-SP: signal peptide of CGTase
LC (Anti-TF): reading frame of the light chain of the anti-TF antibody

DETAILED DESCRIPTION OF THE PREFERRED EMBODIMENT(S)

The text file Sequence_603ST25. txt, created Sep. 21, 2007, and of size 5 kilobytes, filed herewith, is hereby incorporated by reference.

In an embodiment of the present invention, a producing a correctly folded and assembled full-length antibody using an *E. coli* strain is provided. The process of this embodiment comprises fermenting an *E. coli* strain which releases periplasmic proteins into a medium, comprising a gene coding for the heavy chain of an antibody functionally linked to a signal sequence coding for a signal peptide, and a second gene coding for the light chain of an antibody, functionally linked to a signal sequence coding for a signal peptide, in a culture medium, where the *E. coli* strain secretes a full-length antibody into the culture medium. The full-length antibody is removed from the culture medium.

An *E. coli* strain which releases periplasmic proteins into the medium means in the context of the present invention an *E. coli* strain which shows after fermentation a higher concentration of periplasmic proteins in the nutrient medium than the *E. coli* strain W3110 (ATCC 27325).

Particular preference is given to one of the following *E. coli* strains:
 BLR: Novagen
 K802: CGSC* #5610
 WCM100: can be prepared as disclosed in EP0338410B1
 MM28: CGSC* #5892
 RV308: ATCC** #31608; EP0677109B1
 RR1: ATCC** #31434
 *E. coli* strains which are produced as disclosed in EP 497757B1
 leaky mutants of *E. coli* strains
  *can be purchased from the *E. coli* Genetic Stock Center CGSC (830 Kline Biology Tower, MCD Biology Department, 266 Whitney Ave., PO box 208103, Yale University, New Haven),
  **can be purchased from LGC Promochem, Mercatorstr. 51, 46485 Wesel, Germany.

The term leaky mutants encompasses *E. coli* mutants which, owing to mutations in structural elements of the outer cell membrane or of the cell wall, show increased release of periplasmic proteins into the medium (Shokri et al., Appl. Microbiol. Biotechnol., 2003, 60, 654-664). Preferred representatives are *E. coli* strains having a mutation in one of the following genes: omp genes, tol genes, excD gene, excC gene, lpp gene, env genes and lky genes.

Particular preference is given to one of the following *E. coli* strains:
 JF733=CGSC* #6047
 A592=CGSC* #4923
 A593=CGSC* #4924
 A586=CGSC* #4925
 CAG12184=CGSC* #7437
 G11e1=CGSC* #5169
 JE5511=CGSC* #6673
 E610=CGSC* #6669
 E623=CGSC* #6671
 JE5505=CGSC* #6672
 PM61=CGSC* #6628
 PM61R=CGSC* #6629
 JP1228=CGSC* #6703
 207=CGSC* #6686
 AE84064=CGSC* #6575

It is completely surprising that *E. coli* strains which leak periplasmic proteins into the medium can be used to produce full-length antibodies, for the following reason. Secretion of a recombinant protein into the periplasm of *E. coli* normally takes place through the Sec apparatus of the host cell. In this case, the gene of the desired protein is functionally linked to a signal sequence of those proteins which are normally exported by *E. coli* with the aid of the Sec apparatus. After secretion into the periplasm has taken place, the respective signal peptide is eliminated by a signal peptidase (e.g. LepB in the case of *E. coli*). The proteins are therefore transported in the unfolded state through the cytoplasmic membrane. These proteins are then folded and assembled into the correct secondary, tertiary and quaternary structure in the periplasm with the aid of periplasmic chaperones such as, for example, disulfide isomerases (dsb proteins) or peptidylprolyl cis,trans isomerases (e.g. FkpA). This process is particularly complicated in the production of full-length antibodies because in such proteins it is necessary by means of the Sec system for the individual protein chains to be firstly i) transported independently of one another into the periplasm, ii) correctly folded there, and for iii) the intrapeptide disulfide bridges to be correctly formed, iv) two of the light chains to be assembled with two of the heavy chains in the correct form, and v) the interpeptide disulfide bridges to be correctly formed. Those skilled in the art have heretofore assumed to date that the release of the proteins into the medium interferes with such complex folding and assembling processes. Therefore, the release of correctly folded antibodies in a relatively large yield into the fermentation medium is not possible. This is reinforced by the prior art teaching that even if full-length antibodies are produced in the periplasm, high yields of correctly folded antibodies are obtained only if periplasmic chaperones are additionally coexpressed (WO 02/061090).

It has now surprisingly been discovered that when full-length antibodies are produced via the process of the invention even without coexpression of periplasmic chaperones, yields of >160 mg/l of extracellular, correctly folded, assembled and functional antibodies are obtained. The yields can, however, be further increased by coexpression of periplasmic chaperones. Preferred full-length antibodies are antibodies of the IgG and IgM classes, particularly preferably of the IgG class.

For secretion of the light and the heavy chain of antibodies out of the cytoplasm into the periplasm it is necessary for the 5' end of the respective gene of the chain to be produced to be linked in frame to the 3' end of a signal sequence for protein export. Suitable for this purpose are in principle the genes of all signal sequences which make translocation of the target protein possible in *E. coli* with the aid of the Sec apparatus. Various signal sequences are described in the state of the art, for example the signal sequences of the following genes: phoA, ompA, pelB, ompF, ompT, lamB, malE, Staphylococcal protein A, StII and others (Choi & Lee, 2004). Preference is given to the signal sequences of the phoA and ompA genes of *E. coli*, and particular preference is given to the signal sequence for a cyclodextrin glycosyltransferase (CGTase) from *Klebsiella pneumoniae* M5a1 having the sequence SEQ ID NO: 1 (EP 0448093). It is possible in this connection for the genes of the light and heavy chain to be linked at the 5' end to different signal sequences or the same, with preference for linkage to different signal sequences, and particular preference for linkage of one chain to the signal sequence of the phoA or ompA gene of *E. coli* and linkage of the other chain to the signal sequence for a cyclodextrin glycosyltransferase (CGTase) from *Klebsiella pneumoniae* M5a1 having the sequence SEQ ID NO: 1.

The production of DNA molecules which includes a fusion of a signal sequence and the respective gene of the recombinant antibody peptide chain is carried out by methods known to the skilled artisan. Accordingly, the respective gene of the recombinant heavy antibody peptide chain and the respective gene of the light antibody peptide chain can initially be amplified by PCR using suitable oligonucleotides as primers, and subsequently be linked by conventional techniques of molecular biology in each case to a DNA molecule which includes the sequence of a signal peptide and which has been generated in an analogous manner to the gene of the antibody peptide chain, in such a way that an in frame fusion i.e. a continuous reading frame including the signal sequence and the sequence of the respective peptide chain, results. These signal sequence-peptide chain gene fusions can then be either introduced into a vector, e.g. a plasmid, or be integrated directly by known methods into the chromosome of the host cell. It is moreover possible for the fusion gene which comprises the heavy chain, and the fusion gene which comprises the light chain, to be cloned onto two separate but mutually compatible plasmids, or they can be cloned on one plasmid. If both gene fusions are introduced into one plasmid, they can be combined in one operon or they can be expressed in separate cistrons in each case. Preference is given here to combination in one operon, with particular preference for an operon which has, proximal to the transcription start site, the fusion gene comprising the heavy chain of the respective antibody and distally the fusion gene comprising the light chain of the respective antibody. It is possible in the same way for the two gene constructs to be integrated into the chromosome of the host cell combined in one operon or in separate cistrons in each case. Preference is also given here to combination in one operon, with particular preference for an operon which has, proximal to the transcription start site, the fusion gene comprising the heavy chain of the respective antibody and distally the fusion gene comprising the light chain of the respective antibody.

The DNA expression construct consisting of a signal sequence and an antibody peptide chain gene is preferably provided with expression signals which are functional in *E. coli* (promoter, transcription start, translation start, ribosome binding site, terminator).

Suitable promoters are all promoters known to the skilled artisan, such as on the one hand for example inducible promoters such as the lac, tac, trc, lambda PL, ara or tet promoter or sequences derived therefrom. On the other hand, permanent expression is also possible through the use of a constitutive promoter such as, for example, the GAPDH promoter. If the two expression constructs are expressed on different plasmids or on one plasmid in different cistrons, it is possible for this purpose to use identical or in each case one different promoter. Different promoters are preferred.

The expression constructs (promoter-signal sequence-recombinant gene) for the full-length antibody to be produced are then introduced, using methods known to the skilled artisan, into the cells of *E. coli* strains which release periplasmic proteins into the medium.

This takes place for example on a vector, e.g. a plasmid such as, for instance, a derivative of known expression vectors such as pJF118EH, pKK223-3, pUC18, pBR322, pACYC184, pACYC177, pASK-IBA3 or pET. Suitable selection markers for plasmids are genes which code for a resistance to, for example, ampicillin, tetracycline, chloramphenicol, kanamycin or other antibiotics. More preferred antibiotics are tetracycline and kanamycin. If two compatible plasmids are used, normally different selection markers are employed.

The invention also relates to an *E. coli* strain which releases periplasmic proteins into the medium, comprising a gene coding for a heavy chain of an antibody functionally linked to a signal sequence coding for a signal peptide, and a second gene coding for a light chain of an antibody, functionally linked to a signal sequence coding for a signal peptide.

In the *E. coli* strain of the invention, the gene coding for a heavy chain of an antibody functionally linked to a signal sequence coding for a signal peptide, and the second gene coding for a light chain of an antibody, functionally linked to a signal sequence coding for a signal peptide, is preferably further provided with expression signals which are functional in *E. coli*, preferably a promoter, a transcription start, translation start, a ribosome binding site, and a terminator. The expression signals in this case are preferably those previously mentioned above.

The culturing of the cells transformed with the expression plasmid takes place intrinsically by usual fermentation processes known those skilled in the art of bioreactors (fermenters).

The fermentation preferably takes place in a conventional bioreactor, for example a stirred tank, a bubble column fermenter or an airlift fermenter. A stirred tank fermenter is more preferred. In this case, the cells of the protein-producing strain are cultured in a liquid medium over a period of 16-150 h, with continuous monitoring and accurate control of various parameters such as, for example, the nutrient supply, the oxygen partial pressure, the pH and the temperature of the culture. The culturing period is preferably 24-72 h.

Suitable fermentation media are all conventional media known to the skilled artisan for culturing microorganisms. It is possible to use both complex or complete media, or minimal salt media which, in contrast to complete medium, have an accurately defined substrate composition, or minimal salt media to which a certain proportion of complex components such as, for example, peptone, tryptone, yeast extract, molasses or corn steep liquor is added.

It is possible in principle to use as primary carbon source all sugars, sugar alcohols or organic acids or salts thereof which can be utilized by the cells. Preference is given in this connection to the use of glucose, lactose or glycerol. Glucose and lactose are more preferred. Combined feeding with a plurality of different carbon sources is also possible. The carbon source is on the one hand introduced into the medium, e.g. in a concentration of 10-30 g/l, and is then fed in from outside to the culture as required.

The oxygen partial pressure ($pO_2$) in the culture is preferably between 10 and 70% saturation. A $pO_2$ of between 30 and 60% is preferred, and the $pO_2$ is more preferably between 45 and 5% saturation.

The pH of the culture is preferably between pH 6 and pH 8. A pH of between 6.5 and 7.5 is preferably adjusted, and the pH of the culture is more preferably kept at between 6.8 and 7.2.

The temperature of the culture is preferably between 15 and 45° C. A temperature range between 20 and 40° C. is preferred, and a temperature range between 25 and 35° C. is more preferred, and 30° C. is most preferred.

In a preferred embodiment, the temperature is not kept constant during the progress of the fermentation but is reduced for example before inducing gene expression in order to prevent possible formation of inclusion bodies. In such a case, reduction from 30° C. to 25° C. is preferred. A reduction from 30 to 20° C. is more preferred.

The secreted full-length antibody can be purified by known purification methods. Normally, in a first step, the cells are separated from the secreted antibody by separation methods such as centrifugation or filtration. The antibody can be concentrated for example by ultrafiltration and is then purified further by standard methods such as precipitation, chromatography or ultrafiltration. Particularly preferred methods in this connection are those such as affinity chromatography in which the already correctly folded native conformation of the antibody is utilized.

The following example serves to explain the invention further.

All the methods of molecular biology employed, such as polymerase chain reaction, gene synthesis, isolation and purification of DNA, modification of DNA by restriction enzymes, Klenow fragment and ligase, transformation etc. were carried out in the manner known to the skilled artisan, described in the literature or recommended by the respective manufacturers.

EXAMPLE

Fermentative Production of Full-Length Antibodies Using *E. Coli* Secretion Mutants on the 10 l Scale The present example describes the production of the anti-tissue factor (αTF) IgG1 antibody.

The plasmid pJF118ut (FIG. 1) was used as starting vector for cloning and expression of the genes of the anti-(αTF antibody and is deposited at the DSMZ-Deutsche Sammlung von Mikroorganismen und Zellkulturen GmbH (Braunschweig) under the number DSM 18596. pJF118ut is a derivative of the well-known expression vector pKK223-3 (Amersham Pharmacia Biotech) and comprises, besides the β-lactamase gene and the tetracycline-resistance gene, also the tac promoter, which is repressed by the LacIq gene product whose gene is likewise present on the plasmid, and which can be switched on by an inducer such as, for example, D-lactose or isopropyl-β-D-thiogalactopyranoside (IPTG).

The two reading frames for the heavy chain and for the light chain of the anti-αTF antibody, including in each case a signal sequence, were cloned into this plasmid in two consecutive steps.

The procedure for this was as follows:

The DNA fragment with SEQ ID NO: 2 (heavy chain) was produced by gene synthesis and includes a gene fusion consisting of the signal sequence of the ompA gene of *E. coli* and of the reading frame for the heavy chain of the anti-αTF antibody. This DNA fragment was initially cut with the restriction enzymes EcoRI and PstI and ligated to the expression vector pJF118ut, which had been cut with the same restriction enzymes. The plasmid resulting from this cloning, in which the expression of the gene for the heavy chain is under the control of the tac promoter, was called pHC-anti-TF (FIG. 2)

The DNA fragment with SEQ ID NO: 3 (light chain) was likewise produced by gene synthesis and includes a gene fusion consisting of the signal sequence of a CGTase and of the reading frame for the light chain of the anti-αTF antibody. This DNA fragment was initially cut with the restriction enzyme PstI and then ligated to the vector pHC-anti-TF, which had been cut with the same restriction enzyme. The plasmid resulting therefrom was called pAK-anti-TF (FIG. 3). In this way, an artificial operon, which consists of, the respective reading frames for the heavy and the light chain and which is under the control of the tac promoter was generated. Synchronous expression of the two genes is possible by adding an inducer (e.g. IPTG).

To produce the anti-αTF antibody, the strains were transformed in each case with the plasmid pAK-anti-TF by the $CaCl_2$ method. Ampicillin (100 mg/l) was used to select plasmid-containing cells.

Production was carried out in 10 l stirred tank fermenters. The fermenter charged with 6 l of the medium FM4 (1.5 g/l $KH_2PO_4$; 5 g/l $(NH_4)_2SO_4$; 0.3 g/l $MgSO_4 \times 7\ H_2O$; 0.075 g/l $FeSO_4 \times 7\ H_2O$; 1 g/l $Na_3citrate \times 2\ H_2O$; 0.5 g/l NaCl; 1 ml/l trace element solution (0.15 g/l $Na_2MoO_4 \times 2\ H_2O$; 2.5 g/l $Na_3BO_3$; 0.7 g/l $CoCl_2 \times 6\ H_2O$; 0.25 g/l $CuSO_4 \times 5\ H_2O$; 1.6 g/l $MnCl_2 \times 4\ H_2O$; 0.3 g/l $ZnSO_4 \times 7\ H_2O$); 5 mg/l vitamin $B_1$; 3 g/l phytone; 1.5 g/l yeast extract; 10 g/l glucose; 100 mg/l ampicillin) was inoculated in the ratio 1:10 with a preculture which was cultured in the same medium overnight. During the fermentation, a temperature of 30° C. was set and the pH was kept constant at a value of 7.0 by metering in $NH_4OH$ or $H_3PO_4$. Glucose was metered in throughout the fermentation, aiming at a maximum glucose concentration of <10 g/l in the medium. Expression was induced by adding isopropyl β-D-thio-galactopyranoside (IPTG) ad 0.1 mM at the end of the logarithmic growth phase.

Samples were taken after fermentation for 72 hours, and then the cells were separated from the culture medium by centrifugation.

Quantification of the anti-αTF antibody secreted into the culture medium took place by activity determination using an ELISA assay with soluble tissue factor as antigen (coating) and a peroxidase-conjugated goat anti-human $F(ab')_2$ fragment as secondary antibody, as described in Simmons et al. (2002, J. Immunol. Methods 263, 133-47).

The yields of functional anti-αTF antibody determined in this way are listed in Table 1.

TABLE 1

| Anti-αTF antibody yields in the culture supernatant after fermentation for 72 h | |
| --- | --- |
| Strain | Anti-αTF antibody [mg/l] |
| BLR/pAK-Anti-TF | 160 |
| WCM100/pAK-Anti-TF | 240 |
| JF733/pAK-Anti-TF | 170 |
| A592/pAK-Anti-TF | 180 |
| JE5505/pAK-Anti-TF | 160 |
| AE84064//pAK-Anti-TF | 200 |

What is claimed is:

1. A method for producing a correctly folded and assembled full-length antibody using an *E. coli* strain, the method comprising: a) fermenting in a culture medium an *E. coli* strain which leaks periplasmic proteins into a medium, the *E. coli* strain comprising: a gene coding for a heavy chain of an antibody functionally linked to a signal sequence coding for a signal peptide; and a second gene coding for the light chain of an antibody, functionally linked to a signal sequence coding for a signal peptide, wherein the *E. coli* strain secretes a full-length antibody into a culture medium and wherein the leaky mutant is an *E. coli* strain selected from the group consisting of JF733, A592, A593, A586, CAG12184, G11e1, JE5511, E610, E623, JE5505, PM61, 6628, PM61R, JP1228, 207, and AE84064; and b) removing the full-length antibody from the culture medium.

2. The method of claim 1, wherein the antibody is obtained in a yield of greater than 160 mg/l without coexpression of a periplasmic chaperone.

3. The method of claim 1, wherein the signal sequence coding for a signal peptide is selected from the group consisting of the signal sequences of the phoA or ompA gene of *E. coli* or the signal sequence having sequence SEQ ID No: 1.

4. The method of claim 1, wherein the 5' ends of the genes of the light and heavy chain are linked in frame to different signal sequences coding for a signal peptide.

5. The method of claim 4, wherein the 5' end of the gene coding for the one chain of the antibody is functionally linked in frame to the signal sequence of the phoA or ompA gene of *E. coli*, and the 5' end of the gene coding for the other chain of the antibody is linked in frame to the signal sequence SEQ ID No: 1.

6. The method of claim 1, wherein the gene coding for the heavy chain of an antibody functionally linked to a signal sequence coding for a signal peptide, and the second gene coding for the light chain of an antibody, functionally linked to a signal sequence coding for a signal peptide, are combined in one operon.

7. The method of claim 1, wherein fermentation takes place over a period of 16 to 150 hours.

8. The method of claim 1, wherein the fermentation takes place with an oxygen partial pressure ($pO_2$) of between 10 and 70% saturation.

9. The method of claim 1, wherein the fermentation takes place with an oxygen partial pressure ($pO_2$) of between 30 and 60% saturation.

10. The method of claim 1, wherein the fermentation takes place with an oxygen partial pressure ($pO_2$) of between 45 and 55% saturation.

11. The method of claim 1, wherein the pH in the culture medium is between pH 6 and pH 8.

12. The method of claim 1, wherein the pH in the culture medium is between pH 6.5 and 7.5.

13. The method of claim 1, wherein the temperature before induction of gene expression is reduced from 30° C. to 25° C. to prevent formation of inclusion bodies.

14. The method of claim 1, wherein the removal of the full-length antibodies from the culture medium comprises:
 separating the antibodies by centrifugation or filtration,
 concentrating the antibodies by ultrafiltration; and
 purifying the antibodies by precipitation, chromatography or ultrafiltration or affinity chromatography.

* * * * *

SEQUENCE LISTING

```
<160> NUMBER OF SEQ ID NOS: 3

<210> SEQ ID NO 1
<211> LENGTH: 90
<212> TYPE: DNA
<213> ORGANISM: Klebsiella pneumoniae
<220> FEATURE:
<221> NAME/KEY: misc_feature
<223> OTHER INFORMATION: CGTase signal sequence

<400> SEQUENCE: 1
atgaaaagaa accgtttttt taatacctcg gctgctattg ccatttcgat tgcattaaat      60 acttttttt gtagcatgca gacgattgct                                       90
```

<210> SEQ ID NO 2
<211> LENGTH: 1441
<212> TYPE: DNA
<213> ORGANISM: Artificial Sequence
<220> FEATURE:
<223> OTHER INFORMATION: DNA molecule which comprises the gene for the
      heavy chain of the anti-TF antibody
<220> FEATURE:
<221> NAME/KEY: sig_peptide
<222> LOCATION: (24)..(86)
<223> OTHER INFORMATION: mpA signal sequence
<220> FEATURE:
<221> NAME/KEY: allele
<222> LOCATION: (87)..(1430)
<223> OTHER INFORMATION: Gene of the heavy chain of the anti-TF antibody

<400> SEQUENCE: 2

```
cagaattcta aggaggaaat tatatgaaaa agacagctat cgcgattgca gtggcactgg      60
ctggtttcgc taccgtagcg caggctgagg ttcagctggt ggagtctggc ggtggcctgg     120
tgcagccagg gggctcactc cgtttgtcct gtgcagcttc tggcttcaat attaaggagt     180
actacatgca ctgggtccgt caggccccgg gtaagggcct ggaatgggtt ggattgattg     240
atccagagca aggcaacacg atctatgacc cgaagttcca ggaccgtgcc actataagcg     300
ctgacaattc aaaaacaca gcatacctgc aaatgaacag cctgcgtgct gaggacactg     360
ccgtctatta ttgtgctcga gacacggccg cttacttcga ctactggggt caaggaaccc     420
tggtcaccgt ctcctcggcc tccaccaagg gcccatcggt cttccccctg gcaccctcct     480
ccaagagcac ctctggggc acagcggccc tgggctgcct ggtcaaggac tacttccccg     540
aaccggtgac ggtgtcgtgg aactcaggcg ccctgaccag cggcgtgcac accttcccgg     600
ctgtcctaca gtcctcagga ctctactccc tcagcagcgt ggtgactgtg ccctctagca     660
gcttgggcac ccagacctac atctgcaacg tgaatcacaa gcccagcaac accaaggtgg     720
acaagaaagt tgagcccaaa tcttgtgaca aaactcacac atgcccaccg tgcccagcac     780
ctgaactcct ggggggaccg tcagtcttcc tcttcccccc aaaacccaag gacaccctca     840
tgatctcccg gacccctgag gtcacatgcg tggtggtgga cgtgagccac gaagaccctg     900
aggtcaagtt caactggtac gtggacggcg tggaggtgca taatgccaag acaaagccgc     960
gggaggagca gtacaacagc acgtaccgtg tggtcagcgt cctcaccgtc ctgcaccagg    1020
actggctgaa tggcaaggag tacaagtgca aggtctccaa caaagccctc ccagccccca    1080
tcgagaaaac catctccaaa gccaaagggc agccccgaga accacaggtg tacaccctgc    1140
ccccatcccg ggaagagatg accaagaacc aggtcagcct gacctgcctg gtcaaaggct    1200
tctatcccag cgacatcgcc gtggagtggg agagcaatgg gcagccggag aacaactaca    1260
agaccacgcc tcccgtgctg gactccgacg gctccttctt cctctacagc aagctcaccg    1320
tggacaagag caggtggcag caggggaacg tcttctcatg ctccgtgatg catgaggctc    1380
tgcacaacca ctacacgcag aagagcctct ccctgtctcc gggtaaataa taactgcaga    1440
a                                                                    1441
```

<210> SEQ ID NO 3
<211> LENGTH: 771
<212> TYPE: DNA
<213> ORGANISM: Artificial Sequence
<220> FEATURE:
<223> OTHER INFORMATION: DNA molecule which comprises the gene for the
      light chain of the anti-TF antibody
<220> FEATURE:
<221> NAME/KEY: sig_peptide
<222> LOCATION: (26)..(115)

-continued

```
<223> OTHER INFORMATION: CGTase signal sequence
<220> FEATURE:
<221> NAME/KEY: allele
<222> LOCATION: (116)..(760)
<223> OTHER INFORMATION: Gene of the light chain of the anti-TF antibody

<400> SEQUENCE: 3
aactgcagta catggagaaa ataaaatgaa aagaaaccgt ttttttaata cctcggctgc      60
tattgccatt tcgattgcat taaatactt tttttgtagc atgcagacga ttgctgatat     120
ccagatgacc cagtccccga gctccctgtc cgcctctgtg ggcgataggg tcaccatcac    180
gtgcagagcc agtcgcgaca tcaagagcta tctgaactgg tatcaacaga aaccaggaaa    240
agctccgaaa gtactgattt actatgctac tagtctcgct gaaggagtcc cttctcgctt    300
ctctggatcc ggttctggga cggattacac tctgaccatc agcagtctgc aaccagaaga    360
cttcgcaact tattactgtc ttcagcacgg agagtctccg tggacatttg gacagggtac    420
caaggtggag atcaaacgaa ctgtggctgc accatctgtc ttcatcttcc cgccatctga    480
tgagcagttg aaatctggaa ctgcttctgt tgtgtgcctg ctgaataact tctatcccag    540
agaggccaaa gtacagtgga aggtggataa cgccctccaa tcgggtaact cccaggagag    600
tgtcacagag caggacagca aggacagcac ctacagcctc agcagcaccc tgacgctgag    660
caaagcagac tacgagaaac acaaagtcta cgcctgcgaa gtcacccatc agggcctgag    720
ctcgcccgtc acaaagagct tcaacagggg agagtgttaa tagctgcaga a             771
```